US008715358B2

(12) United States Patent
Masini (10) Patent No.: US 8,715,358 B2
(45) Date of Patent: May 6, 2014

(54) PCL RETAINING ACL SUBSTITUTING TKA APPARATUS AND METHOD

(76) Inventor: Michael A. Masini, Ann Arbor, MI (US)

( * ) Notice: Subject to any disclaimer, the term of this patent is extended or adjusted under 35 U.S.C. 154(b) by 436 days.

(21) Appl. No.: 12/175,715

(22) Filed: Jul. 18, 2008

(65) Prior Publication Data

US 2010/0016977 A1 Jan. 21, 2010

(51) Int. Cl.
*A61F 2/38* (2006.01)
(52) U.S. Cl.
USPC ............... 623/20.21; 623/20.27; 623/20.23; 623/20.31; 623/20.28
(58) Field of Classification Search
USPC ...................................................... 623/20.21
See application file for complete search history.

(56) References Cited

U.S. PATENT DOCUMENTS

| | | | |
|---|---|---|---|
| 4,213,209 A | 7/1980 | Insall et al. | |
| 4,298,992 A | 11/1981 | Burstein et al. | |
| 5,133,758 A | 7/1992 | Hollister | |
| 5,326,361 A | 7/1994 | Hollister | |
| 5,413,604 A | 5/1995 | Hodge | |
| 5,871,541 A * | 2/1999 | Gerber | 623/20.29 |
| 6,123,729 A | 9/2000 | Insall et al. | |
| 6,190,415 B1 | 2/2001 | Cooke et al. | |
| 6,443,991 B1 | 9/2002 | Running | |
| 6,582,469 B1 * | 6/2003 | Tornier | 623/20.27 |
| 6,589,283 B1 | 7/2003 | Metzger et al. | |
| 6,797,005 B2 | 9/2004 | Pappas | |
| 6,905,513 B1 | 6/2005 | Metzger | |
| 6,926,738 B2 | 8/2005 | Wyss | |
| 6,986,791 B1 * | 1/2006 | Metzger | 623/20.24 |
| 7,255,715 B2 | 8/2007 | Metzger | |
| 2001/0003803 A1 * | 6/2001 | Leclercq | 623/20.29 |
| 2003/0004577 A1 | 1/2003 | Running | |
| 2003/0199985 A1 | 10/2003 | Masini | |
| 2004/0143339 A1 * | 7/2004 | Axelson et al. | 623/20.21 |
| 2004/0162620 A1 | 8/2004 | Wyss | |
| 2004/0193279 A1 | 9/2004 | Roger | |
| 2004/0243244 A1 | 12/2004 | Otto et al. | |
| 2005/0119661 A1 * | 6/2005 | Hodgson et al. | 606/90 |
| 2005/0143832 A1 | 6/2005 | Carson | |
| 2005/0187635 A1 | 8/2005 | Metzger | |

(Continued)

OTHER PUBLICATIONS

The Journal of Arthroplasty, vol. 20 (Jan. 2005) The Early Innovators of Today's Resurfacing Condylar Knees by Raymond P. Robinson, MD, FACS.
The Journal of Bone and Joint Surgery, Inc., 1999, Total Knee Arthroplasty with Retention of Both Cruciate Ligaments. A Nine to Eleven-Year Follow-up Study by J.M. Cloutier, M.D., F.R.C.S.(C); P. Sabouret, M.D., C.S.P.Q. and A. Deghrar, M.D.; Montreal, Quebec, Canada.

(Continued)

*Primary Examiner* — David Isabella
*Assistant Examiner* — Jacqueline Woznicki
(74) *Attorney, Agent, or Firm* — Eugene M. Cummings, P.C.

(57) ABSTRACT

A new class of total knee replacement includes a posterior cruciate ligament retaining anterior cruciate ligament substituting apparatus and method. Particular design considerations include: 1) a specific extension surface separate from the flexion surface, 2) rotational control in full extension to create the so-called screw-home mechanism, 3) translation restraints that will substitute for ACL function including a CAM-post or other abutment mechanism while allowing normal PCL function which should improve natural proprioception, 4) a modified femoral component with separate radii of curvature for the flexion and extension arcs of at least one condyle, and 5) a tibial component with slope built into the posterior aspect of its bone contacting surface on both sides of the PCL.

10 Claims, 8 Drawing Sheets

(56) References Cited

U.S. PATENT DOCUMENTS

| | | |
|---|---|---|
| 2006/0190086 A1 | 8/2006 | Clemow et al. |
| 2006/0265080 A1 | 11/2006 | McMinn |
| 2007/0135925 A1 | 6/2007 | Walker |
| 2007/0135926 A1 | 6/2007 | Walker |
| 2007/0198022 A1 | 8/2007 | Lang et al. |
| 2008/0097615 A1* | 4/2008 | Lipman et al. ............. 623/20.27 |
| 2009/0036992 A1* | 2/2009 | Tsakonas ................... 623/20.14 |
| 2009/0210066 A1* | 8/2009 | Jasty ......................... 623/20.31 |
| 2009/0265014 A1* | 10/2009 | May et al. .................. 623/20.21 |
| 2009/0306783 A1* | 12/2009 | Blum ......................... 623/20.21 |
| 2009/0306784 A1* | 12/2009 | Blum ......................... 623/20.21 |
| 2009/0319048 A1* | 12/2009 | Shah et al. ................. 623/20.29 |

OTHER PUBLICATIONS

Ortho SuperSite—Effect of ACL Sacrifice, Retention, or Substitution on Kinematics After TKA by Michael D. Ries, MD, Aug. 2007, http://www.orthosupersite.com/print.asp?rID=23134.

* cited by examiner

PCL RETAINING ACL SUBSTITUTING TKA APPARATUS AND METHOD

FIELD OF THE INVENTION

The present invention relates generally to arthroplasty and more particularly to total knee arthroplasty ("TKA"). More specifically, this invention relates to an apparatus and method of knee replacement surgery wherein the posterior cruciate ligament ("PCL") is retained while the anterior cruciate ligament ("ACL") is substituted for.

DESCRIPTION OF THE PRIOR ART

Knee replacement surgery, though effective for pain, has traditionally been unable to result in significantly normal functional improvement in joint mobility. In the history of total knee replacement, there is a long track record of providing improved pain relief for patients with advanced arthritic change of the knee. In these procedures, usually a femoral component is used to resurface the end of the distal femur and a tibial component is used to resurface the proximal portion of the tibial. Similarly, a patellar component may be used to resurface the patella. Basically, the ends of the bone are cut using both alignment and cutting guides and then the components are cemented in place or perhaps are used in the uncemented mode with some type of bone fixation attached to the metal component.

In general, these methods have been either (i) PCL retaining; or (ii) PCL sacrificing or substituting. As to the former, PCL retaining devices have been used whereby the PCL has been retained. These, however, all essentially function with ACL deficiency either due to prior existing deficiency or surgical removal at the time of TKA. Although pain relief is improved, function is sacrificed.

By contrast, U.S. Pat. No. 4,213,209 to Insall et al., the complete disclosure of which is incorporated by reference herein, disclosed the concept of a PCL substituting device using a CAM on the femoral component and a post on the tibial component. Subsequent work by others have used similar mechanisms to try to replace the function of the PCL. Some devices have further used a hinged type mechanism to lock the two components together. In other words, the tibial and femoral components are held together by some type of hinge mechanism. These have been significantly less successful than resurfacing devices due to the increased constraint placed on the bone and thus most studies have shown a higher incidence of loosening. Still other mechanisms have also been employed that substitute for the PCL while sacrificing the ACL, such as using a femoral sphere and a tibial recessed cavity.

Other devices have been designed to retain both the ACL and the PCL. The early use of such types of designs employed mechanisms whereby the cruciate ligaments are retained on a block of bone in the central portion of the tibia. More recently, U.S. Pat. No. 6,903,513 to Metzger, the complete disclosure of which is incorporated by reference herein, disclosed the concept of combining a total knee replacement with ligament reconstruction.

Most recently, devices have been designed on the concept of "bicruciate substituting". One example of which includes a post and CAM for the PCL and an anterior post engagement point in early hyperextension to provide for the ACL's function of resisting hyperextension.

Unfortunately, in all current devices and methods, the function of the ACL has been sacrificed or the balancing of the knee with retention of both ligaments has been difficult to achieve. The result has been implants which generally function insufficiently for high levels of activity, especially sports, due to either a mismatch between the flexion and extension gaps due to excessive ligament tightening or loosening or irregular bone cuts and/or instability due to ligament deficiency.

OBJECTS OF THE INVENTION

Accordingly, it is an object of this invention to provide a knee replacement which is significantly more functional than currently existing devices allowing for more normal range of motion and function.

Another object of this invention is to provide a knee replacement whereby the PCL is retained and the ACL is substituted for.

A more specific object of this invention is to use articular geometry and an anterior located CAM post type mechanism to provide a knee replacement whereby the function of the ACL will be substituted while still maintaining the PCL allowing it to perform its normal function including improved proprioception and roll back.

Another object of this invention is to provide a knee replacement which not only provides significant improvement relative to pain but also, and perhaps more importantly, improved function and mobility for high levels of activity including sports.

These and other objects and advantages of this invention will be apparent from the detailed description and drawings. What follows is a preferred embodiment of the present invention. To assess the full scope of the invention the claims should be looked to as the preferred embodiment is not the only embodiment within the scope of the invention.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE ILLUSTRATED EMBODIMENT

Figure 1:
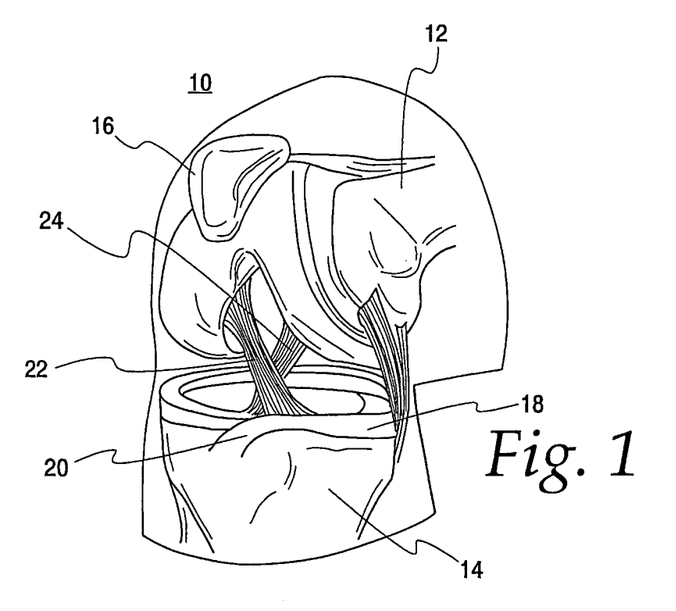
FIG. 1 is a perspective view of a right knee joint.
Figure 2A:
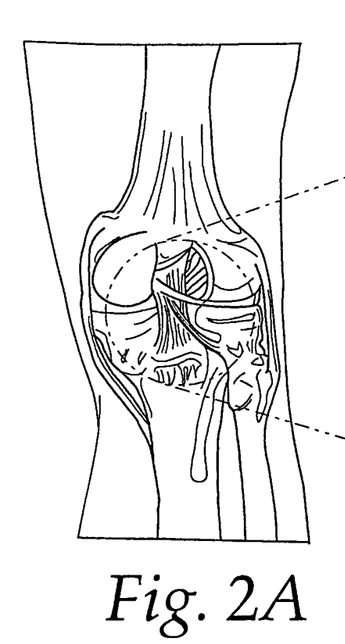
FIG. 2A is a posterior view of FIG. 1.
Figure 2B:
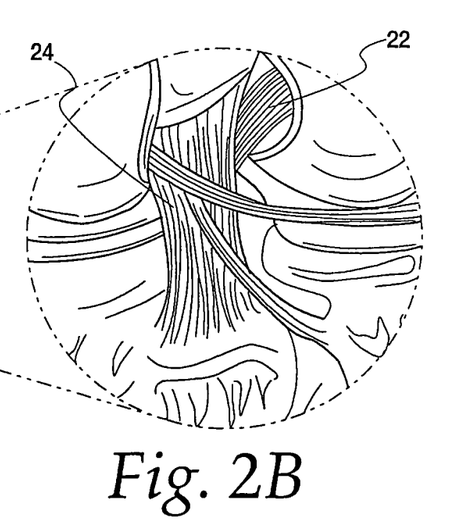
FIG. 2B is an exploded view of FIG. 2A.

Turning now to the Figures, FIG. 1 is illustrative of a human knee joint 10. The knee is a lower extremity joint connecting the femur 12 and the tibia 14, with the patella 16 riding the joint as the knee bends. Between the bones of the femur 12 and tibia 14 is a structure made of cartilage, called the meniscus 18. The meniscus is a C-shaped piece of tissue attached to the tibia via the meniscal ligament 20 and helps to protect the joint and allows the bones to slide freely on each other. The bones themselves are coated with a different type of cartilage called hyaline cartilage which forms the joint surface on each bone respectively. There are two cruciate ligaments located in the center of the knee joint. The anterior cruciate ligament (ACL) 22 and the posterior cruciate ligament (PCL) 24 (see also FIGS. 2A and 2B) are the major stabilizing ligaments of the knee. The ACL 22 prevents the femur 12 from sliding backwards on the tibia 14 (or the tibia sliding forwards on the femur), while the PCL 24 prevents the femur 12 from sliding forward on the tibia 14 (or the tibia from sliding backwards on the femur). Both the ACL and the PCL stabilize the knee in a rotational fashion as well.

Figure 3A:
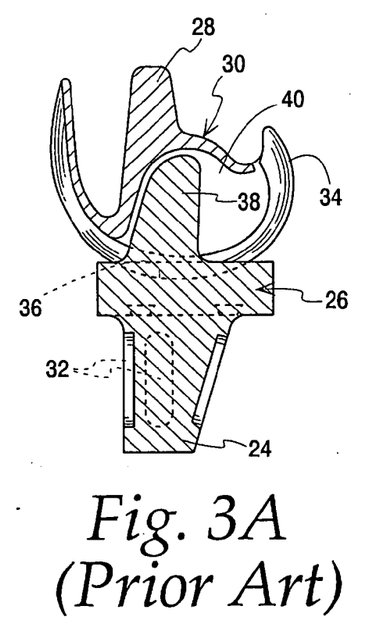
FIGS. 3A-3C are side cross-sectional views illustrating a prior art CAM and post PCL substituting knee replacement.
Figure 3B:
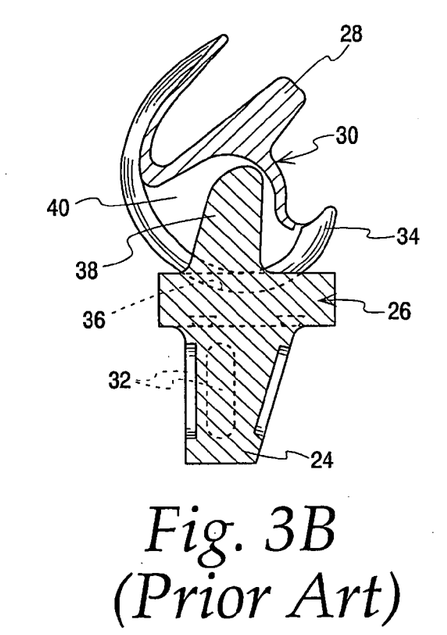
Figure 3C:
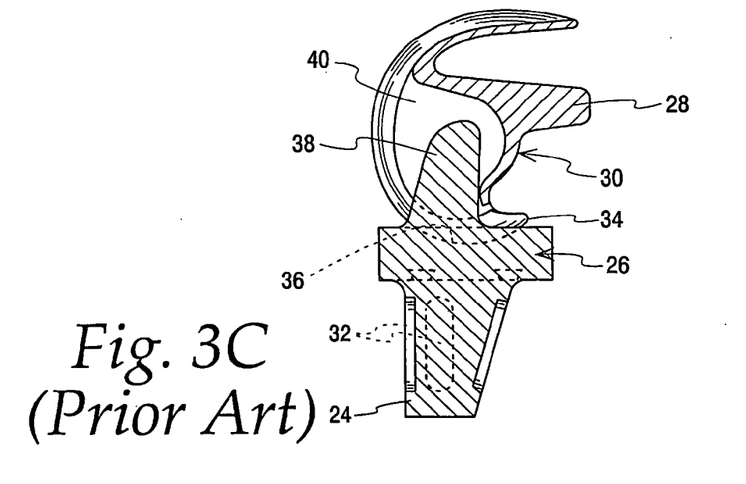

Advanced arthritic change in the knee, other diseases, or damaged/injured joint and/or ligaments may require a TKA. FIGS. 3A-3C illustrate a prior art CAM and post style PCL substituting TKA. The components of this type of TKA, such as that described by FIGS. 3A-3C, are implanted in the femur and tibia by a surgical procedure which involves resection of bone on condyles of the femur and tibia and formation of holes to receive the respective component posts. In particular, the tibia fixation post 25 of the tibial component 26 is implanted into the hole formed in the tibia while the femoral fixation post 28 of the femoral component 30 is implanted into the hole formed in the femur. Both components are then durably affixed to the bones by surgical cement which may be anchored via slots 32 in the components. Cementless fixation with press-fit or bone growth surfaces are also well known in the art.

This prosthesis permits a relatively wide range of motion, from extension in FIG. 3A on through FIG. 3B to approaching flexion of ninety degrees in FIG. 3C. In all positions, the external surfaces of the condylar portions 34 of the femoral component 30 rotate in the concavities 36 of the tibial component 26, while the engagement post 38 of the tibial component 26 extends up into the intercondylar recess 40 of the femoral component 30. This CAM and post style PCL substituting TKA provides good pain relief but has been associated with mechanical problems such as patellar clunk syndrome, mid-flexion instability, decreased motion, excessive post wear, and generally poorer than normal function.

Turning now to the general principles of the present invention wherein an improved knee replacement retains the PCL and substitutes the ACL. This substitution includes several possible embodiments (infra), including a CAM and post mechanism which is designed to interact anterior to the location of the PCL, thereby allowing the PCL to perform its normal function while the CAM post mechanism performs the function of the ACL. Additionally, surface geometry may be created such that additional slope is applied into the proximal tibia to enhance flexion during knee range of motion.

Stability during mid-flexion is a key component of sports activities and mid-flexion instability is a major cause of abnormal function in prior art TKA. Additionally, a biconvex distal femoral surface may be created to articulate with a correspondingly concave, convex, or flat tibial proximal tibial surface to enhance stability in terminal extension.

Figure 4:
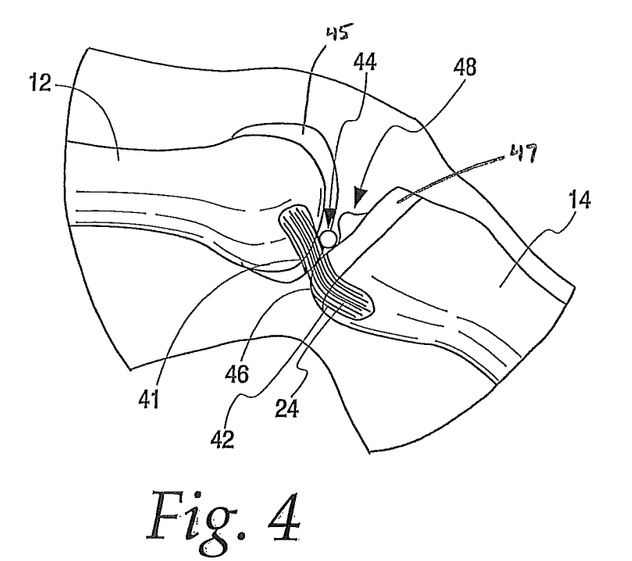
FIG. 4 is a lateral view of an embodiment of the present invention wherein the PCL is retained and the ACL is substituted with a femoral CAM and tibial post.

More particularly and referring now to FIG. 4, a preferred embodiment of the present invention is shown. In this embodiment, a central passageway 41 is provided in the femur, and a posterior recess 42 is provided in the tibia 14 for the PCL 24. On the femoral portion of the design, a CAM 44 is provided on the femoral component 45 which is designed to engage some portion of the tibial surface 46 to help prevent translation (or paradoxical movement) of the femur 12 on the tibia 14 at the initiation of flexion. The aim of this CAM 44 and post 48 design is to prevent this early translation while allowing the PCL to perform its function as flexion proceeds allowing the normal roll back of the femur 12 on the tibial component. The CAM/post (ACL substitution) engagement also facilitates rotation such that either a convex or concave anterior CAM surface engages with a correspondingly concave or convex posterior tibial post surface. The tibial post 48 is designed such that it is relatively low in profile so that as flexion proceeds to deep flexion, the patella 16 will not impinge on the most proximal portion of the post. It should be apparent to those familiar with the art that the invention is meant to be part of a system with multiple sizes of both the femoral and tibial components to accommodate different patient sizes and gender as well as providing modularity with varying thicknesses of tibial inserts and so forth.

Figure 5:
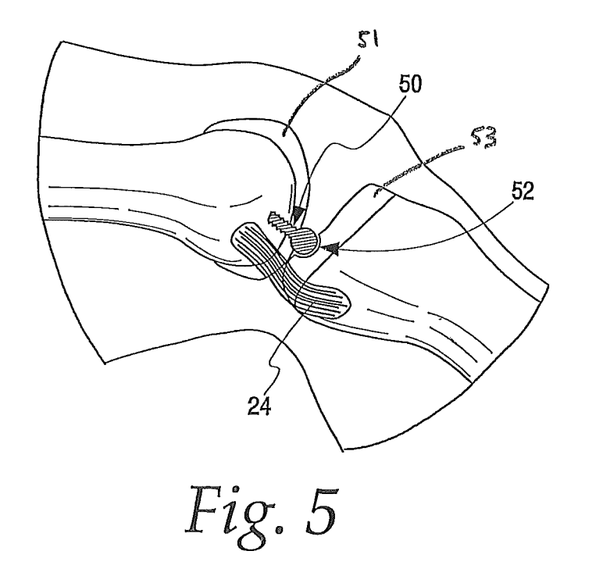
FIG. 5 is a lateral view of an alternate embodiment of the present invention wherein the PCL is retained and the ACL is substituted with a femoral spherical protrusion and a tibial recess.

A slight variation of the embodiment of FIG. 4 is shown in FIG. 5. Here the intercondylar element on the femoral component is a spherical femoral protrusion 50 of the femoral component 51, which engages the intercondylar mating element on the tibial component, or a tibial posterior recess 52, of the tibial component 53 to substitute for the ACL. More specifically, the preferably circular projection engages a concave hemisphere on the corresponding tibial component 53 and, thus serves also to function to prevent translation until the PCL can again proceed with its function. It will be obvious to those familiar with the art that any number of different types of CAM/post mechanisms can be used to provide engagement. Most importantly, as opposed to the prior art, the engagement here is to prevent early translation due to a deficient or completely absent ACL while simultaneously maintaining the presence of the PCL 24.

FIGS. 6 and 7A-C illustrate lateral, AP, and oblique views of another inventive embodiment of the invention which may be employed separately or in concert with other elements of the invention. The ACL is known to prevent hyperextension as well as to control translation and rotational movements about the knee. The regions shaded in FIGS. 6 and 7A-7C represent areas with differing radii of curvature (see curves of surfaces 54, 56 and 62 of FIG. 6) on the femoral component and correspondingly on the tibial insert which are meant to contact in terminal extension and functionally limit continued extension/hyperextension—a function normally performed by an intact native ACL.

Figure 6:
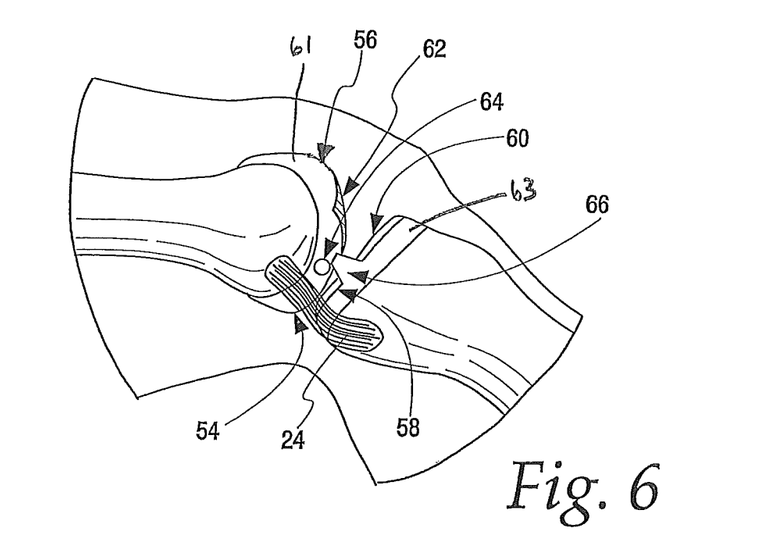
FIG. 6 is a lateral view of another embodiment of the present invention wherein the femoral condylar surface of at least one condyle has two radii of curvatures in the sagittal plane.
Figure 7A:
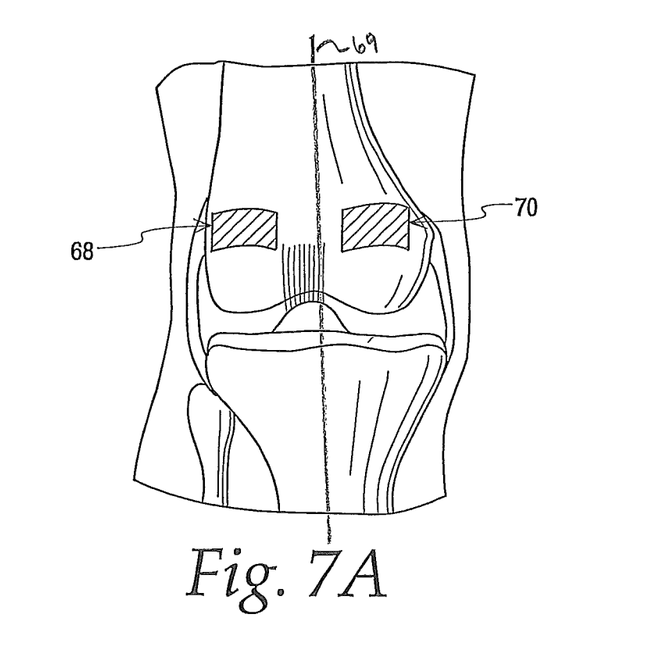
FIGS. 7A-7C are frontal, oblique and lateral views, respectively, of the biconvex distal femoral condyles.

More particularly, FIG. 6 shows an alternate embodiment of the present invention wherein the femoral condylar surface of at least one condylar has two separate radii, 54 and 56, in the sagittal plane (see FIG. 7A). One surface 54 for contact from about 20 degrees of flexion to full flexion and a separate surface 56 for contact from about 20 degrees of flexion to full extension. The tibial articulating surface of the tibial component 63 would have corresponding contacting surfaces depicted at 58 and 60 respectively. The shaded area 62 indicates the difference from current prior art femoral implants (wherein the sagittal radius of area 56 would transition smoothly into the sagittal radius of area 54 whether or not the radius were the same—single radius, or different—multi-radius as are well known in the art). The retained PCL is depicted at 24 and the CAM/post ACL substituting mechanism at 64/66 respectively. The region of articular tibial buildup that will guide external rotation for the "screw home" mechanism (infra) in terminal extension is indicated at 60.

Figure 7B:
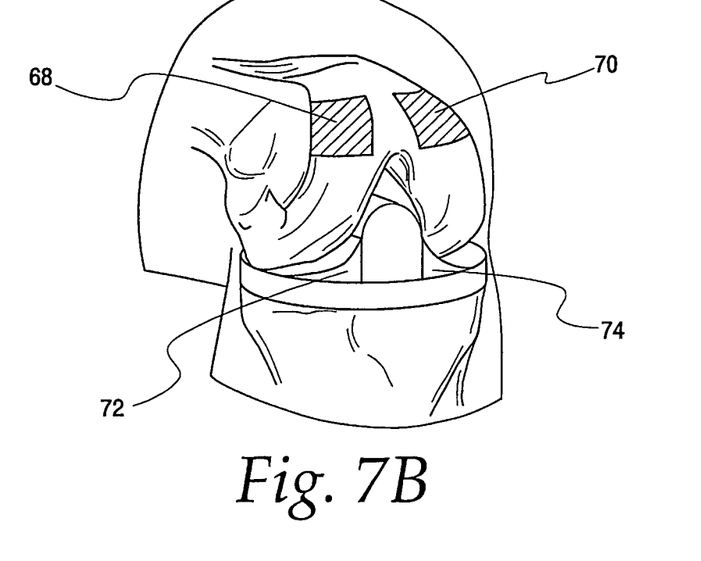
Figure 7C:
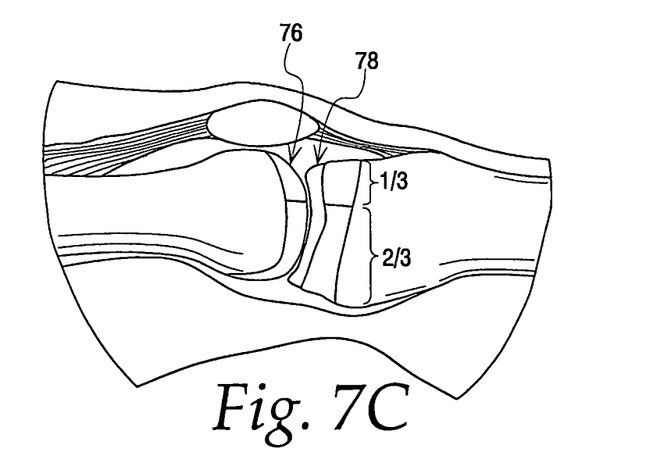

FIGS. 7A-7C illustrate frontal, oblique and lateral views, respectively, of the biconvex distal femoral condyles. In particular, and referring to FIGS. 7A and 7B, shaded areas 68 and 70 indicate the medial and lateral femoral extension contact areas with corresponding tibial articulating mating areas at 72 and 74. While FIG. 7C shows a lateral view of either a medial or lateral condyle with the femoral extensor convex surface at 76 and the corresponding tibial surface at 78.

Accordingly, a radius of curvature in FIGS. 7A and 7B at 68 on the medial side and 70 on the lateral side will preferably have radius of curvature greater than the flexion radius though a lesser radius of curvature would be possible as well. The corresponding radius of curvature of the tibia could be concave, flat, or even convex as desired. These are specifically designed to contact the extensor surface of the tibial components. As shown in FIG. 7C, this surface generally would be approximately ⅓ of the anterior posterior dimension of the tibial surface. The femoral component therefore has corresponding regions in the sagittal plane with distinct radii of curvature—a posteriorly located region for flexion and an anterior region for the knee as it approaches extension. The knee could also have an additional smaller radius at its most posterior region as is known in the art for current so-called high flexion knees.

The tibial surface would thus have a more concave posterior section for flexion and a separate articulating extensor surface. This will facilitate normal motion and function to replace the deficient ACL. In fact, this is found in a natural and healthy knee joint where (in the lateral profile) a relatively defined arc of curvature actually starts at about ⅓ of the distal femur particularly on the lateral femoral condyle—as seen in X-rays and/or MRI film.

Turning back to FIG. 6, there is provided an extensor surface to provide additional function that the ACL provides. Whether just medially, or laterally and centrally as well, a surface is created, and it is the anterior portion of the tibial component which is meant as an articular bearing surface in full extension. The ACL also helps to prevent hyperextension and is a limiting structure in extension in which these surface(s) will serve to provide that function. Accordingly, as opposed to traditional knee replacements where the articulating portion of the surface covers the entire tibia, the present invention utilizes the tibial articular surfaces essentially divided into portions which function for flexion as well as portions which function as extensor articulating surfaces. Additionally, FIG. 6 further shows an articulation which can be included to enhance external rotation of the femur on the tibial in terminal extension. This is the so-called screw-home mechanism of the knee. This region 60 will facilitate, as the knee comes into full extension, an external rotational motion and thus recreate the normal kinematics of the knee.

Figure 8:
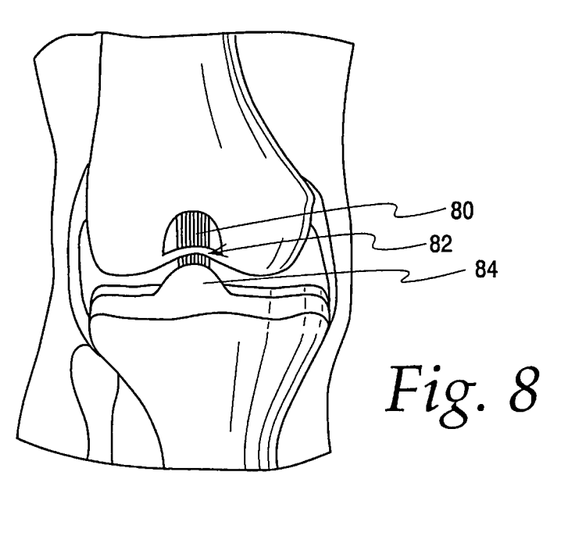
FIG. 8 is frontal view of an embodiment of the present invention.

FIG. 8 shows an end-on or frontal view of the present invention showing the PCL at 80 and the anterior cruciate CAM at 82. The CAM 82 passes anterior to the ligament 80 in extension and distal to the ligament 80 in flexion. In this ACL substitution mechanism, a CAM 82 and post 84, pass anterior/distal to the PCL. The ACL is thus substituted for while the PCL is retained in its anatomic position. Other mechanisms for substitution may include a femoral sphere and tibial recess or any other mechanical abutment mechanism which would inhibit femoral anterior translation on the tibial surface during early flexion until the PCL becomes taut and exhibits its normal tensioning function and leads to femoral rollback as flexion progresses.

Figure 9:
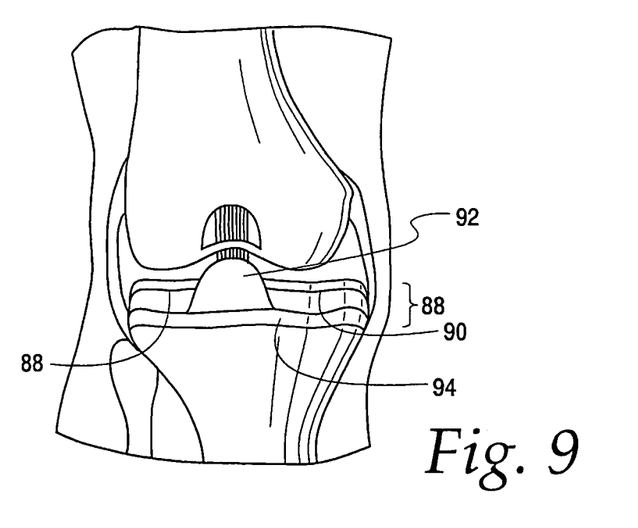
FIG. 9 is a frontal view with separate medial and lateral tibial inserts as opposed to a single insert.

FIG. 9 shows an alternative embodiment whereby the tibial insert 86 is modular to permit separate medial 88 and lateral 90 inserts. This is particularly beneficial for the invention as retaining the PCL may lead to inequality of the lateral and medial joint spaces in flexion/extension or both. The central post 92 could be a separate insert, a permanent portion of the tibial tray 94 or included with either the medial 88 or lateral 90 insert. This will allow fine tuning of the medial and lateral flexion and extension spaces. Such a feature may be desirable as the increased constraint, which would be present by substituting for the ACL, could be difficult to balance. In fact, such a feature may also be desirable in currently existing TKAs, and especially posterior cruciate retaining knees. It should be apparent to those familiar with the art that mobile bearings, either separate medial or lateral or a single rotating or sliding bearing could be used.

Figure 10A:
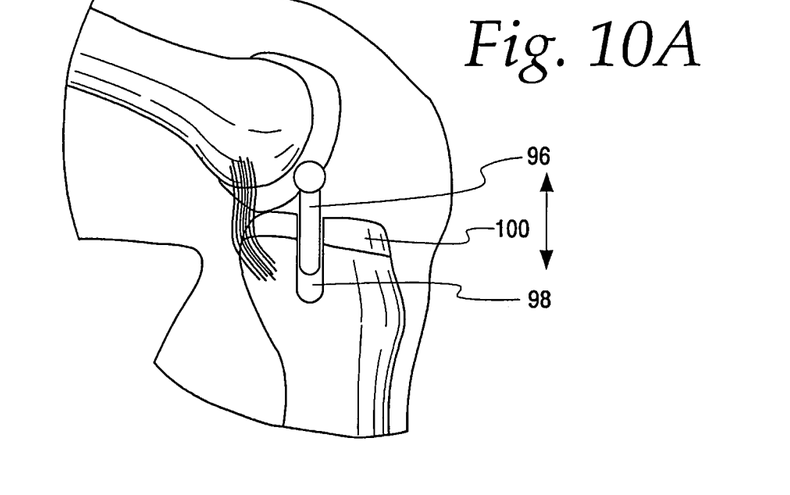
FIGS. 10A-10C are alternate embodiments of the tibial post wherein the post may move in one or more directions within the tibial baseplate.
Figure 10B:
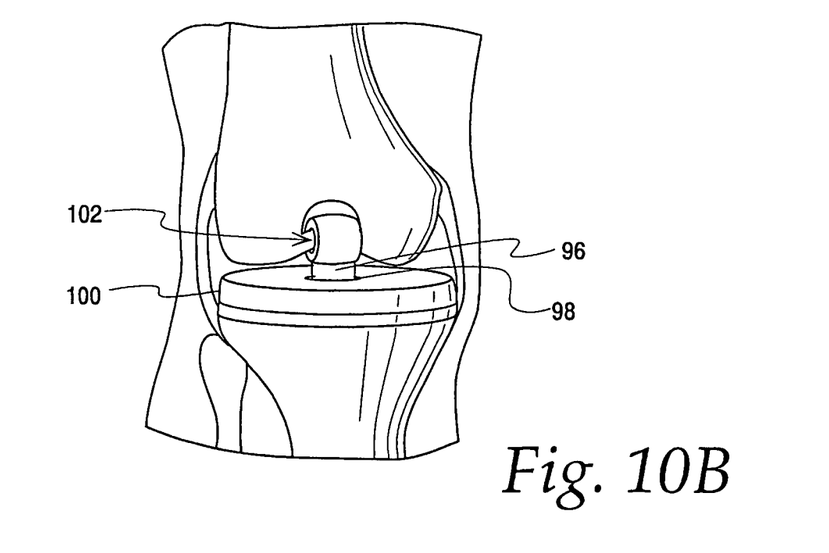
Figure 10C:
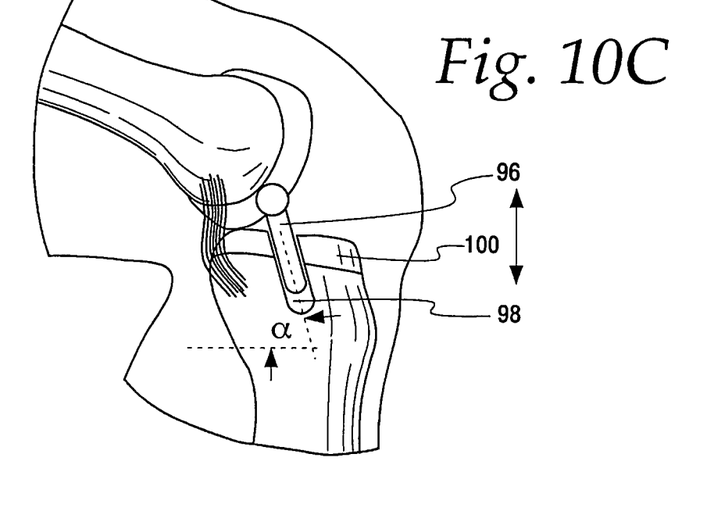

FIGS. 10A-10C depict alternate embodiments whereby mobile cam/post components exist as part of the design. These embodiments show the tibial post is a rod 96 that may move in one or more dimensions within a tubular opening 98 in the tibial baseplate 100. This mechanism would provide translational constraint to the femoral-tibial joint while permitting rotational freedom and axial motion as the knee moves through flexion. FIG. 10B shows a frontal view of the mechanism which could also have a rotating tibial bearing as known in the art. FIG. 10C shows an alternative embodiment whereby the tibial tubular mechanism is slanted or angled posteriorly with respect to the tibia to facilitate femoral rollback as the knee moves through flexion. The rod portion would attach to the femoral CAM as part of a modified hinge mechanism 102 that would have axial and rotational freedom. Angle alpha would exist between the baseplate and the tubular tibial extension.

Figure 11:
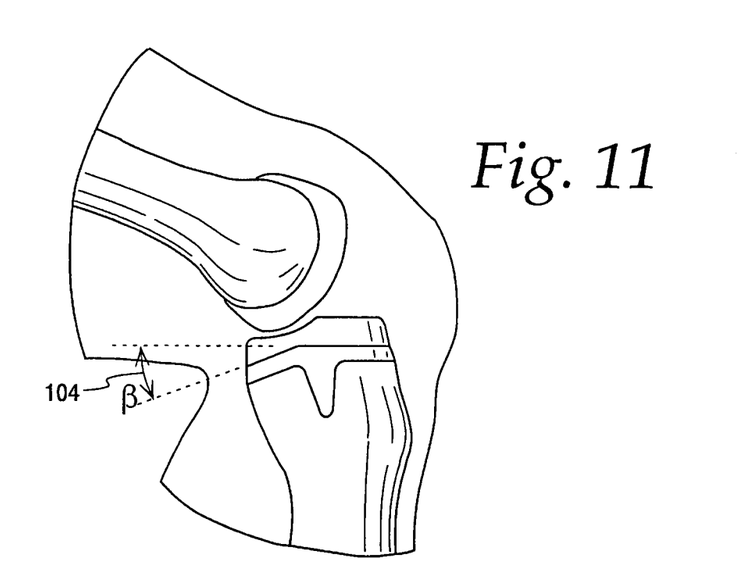
FIG. 11 is another alternate embodiment of the present invention whereby slope is integral to the tibial component.

FIG. 11 shows an alternate embodiment whereby tibial slope is built into a portion of the tibial component. In this embodiment, an angle, beta 104 exists between two portions of tibial bone contacting surface of the tibial implant such that additional posterior slope is built into the component itself. Such a design will facilitate additional flexion through range of motion while providing a more favorable mechanical interface between implant and bone. The enhanced slope itself of the posterior aspect of the tibia will serve as a mechanism to inhibit early anterior translation of the femoral component relative to the tibial component.

The interface as shown in FIG. 11 will provide a portion which is generally perpendicular to the long axis of the bone and an oblique interface posteriorly which will facilitate enhanced flexion and a thicker, more congruent bearing insert posteriorly then would be possible with a planar tibial implant. The central portion would have a recess to allow the maintenance of a bone block to avoid injury to the insertion of the PCL. As opposed to wedges/augments as are familiar to the art, the slope is oriented posteriorly to facilitate flexion while still permitting a transverse mating surface for stability of the implant at the bone/implant interface. The enhance slope will facilitate improved flexion with less "lipping" posteriorly of the insert and could provide an articular mating surface canted posteriorly approximately 10 to 20 degrees which would provide a more physiologic surface for sports activities. Again, a separate extension surface could also be provided with separate radii of curvature on the femoral or tibial components or both. It should be apparent that this angled posterior tibial baseplate is inventive in its own right and could be employed even in currently existing PCL retaining and sacrificing or substituting designs.

The foregoing description of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed is:

1. A total knee implant system for replacing the articulating portion of a femur and a tibia while substituting for the function of an absent anterior cruciate ligament and allowing for the retention of the posterior cruciate ligament without the posterior cruciate ligament contacting a posterior aspect of the implant, the implant comprising:
    a femoral component having medial and lateral condyles, said femoral component having a central passageway adapted to receive the posterior cruciate ligament;
    a tibial component having a recess adapted to receive the posterior cruciate ligament;
    an intercondylar element bridging said condyles transversely and forming a transverse cam on the femoral component, wherein said element is located anterior to the central passageway to receive the posterior cruciate ligament to prevent impingement of the ligament against the intercondylar element; and
    an intercondylar mating surface on the tibial component for contacting the intercondylar element of the femoral component during at least a portion of an arc of motion of the total knee implant system wherein said transverse cam contacts a posterior surface of said mating surface thereby enabling generally normal function of the posterior cruciate ligament wherein said recess adapted to receive the ligament passes posterior to said element.

2. The total knee implant system of claim 1 wherein the intercondylar element of the femoral component is a CAM.

3. The total knee implant system of claim 2 wherein the CAM rotates within the femoral component.

4. The total knee implant system of claim 1 wherein the intercondylar mating surface of the tibial component is a post.

5. The total knee implant system of claim 4 wherein the post rotates within the tibial component.

6. The total knee implant system of claim 1 wherein the intercondylar mating surface of the tibial component contacts the intercondylar element after the initiation of flexion of the knee.

7. The total knee implant system of claim 1 wherein the intercondylar element of the femoral component has a spherical mating surface.

8. The total knee implant system of claim 1 wherein the intercondylar mating surface on the tibial component is a recess.

9. The total knee implant system of claim 1 wherein the femoral component includes a condylar surface having at least two radii of curvature in the sagittal plane, one of said radii allows contact of said condylar surface with said mating element when the knee is in extension and another of said radii allowing contact of said condylar surface with said mating element when the knee is within the major arc of flexion.

10. The total knee implant system of claim 1 wherein the tibial component includes a mobile bearing.

* * * * *